(12) United States Patent
Sista et al.

(10) Patent No.: US 8,530,685 B1
(45) Date of Patent: Sep. 10, 2013

(54) MONODENTATE GOLD ETHYNYL COMPLEXES

(75) Inventors: Srinivas Prasad Sista, Glenville, NY (US); Arunkumar Natarajan, Niskayuna, NY (US); Jie Jerry Liu, Niskayuna, NY (US); Patrick Joseph McCloskey, Watervliet, NY (US); Joseph John Shiang, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 13/561,159

(22) Filed: Jul. 30, 2012

(51) Int. Cl.
*C07F 1/12* (2006.01)
*H01L 51/00* (2006.01)
*C09K 11/06* (2006.01)

(52) U.S. Cl.
USPC .... 556/22; 257/40; 257/E51.044; 252/301.18

(58) Field of Classification Search
USPC ......... 556/22; 257/40, E51.044; 252/301.18
See application file for complete search history.

(56) References Cited

U.S. PATENT DOCUMENTS

| | | | |
|---|---|---|---|
| 7,572,912 B2 | 8/2009 | Yam et al. | |
| 7,582,363 B2 | 9/2009 | Takahashi et al. | |
| 7,834,135 B2 | 11/2010 | Tsuboyama et al. | |
| 8,063,554 B2 | 11/2011 | Holmes et al. | |
| 2006/0009629 A1 | 1/2006 | Takahashi et al. | |
| 2006/0091378 A1 | 5/2006 | Yam et al. | |
| 2009/0091243 A1 | 4/2009 | Fujimura et al. | |
| 2010/0140605 A1 | 6/2010 | Shibata et al. | |
| 2010/0237770 A1 | 9/2010 | Fujimura et al. | |
| 2011/0012093 A1 | 1/2011 | Yam et al. | |
| 2011/0101327 A1 | 5/2011 | Stoessel et al. | |

OTHER PUBLICATIONS

Chui et al., Chem. Eur. J., vol. 11, pp. 1739-1749 (2005).*

* cited by examiner

*Primary Examiner* — Porfirio Nazario Gonzalez
(74) *Attorney, Agent, or Firm* — Mary Louise Stanford

(57) ABSTRACT

Monodentate gold ethynyl complexes having a gold-carbon bond and a gold-phosphorous bond, specifically, of formula I, may be useful in optoelectric devices,

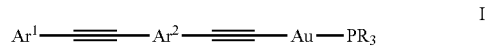

wherein $Ar^1$ and $Ar^2$ are independently monocyclic or polycyclic aryl, unsubstituted or substituted with one or more alkyl, alkenyl, alkoxy, aryl, aryloxy, fluoro, fluoroalkyl, or perfluoroalkyl; and R is substituted or unsubstituted aryl.

21 Claims, 2 Drawing Sheets

MONODENTATE GOLD ETHYNYL COMPLEXES

BACKGROUND

Ongoing challenges for organic light emitting diodes (OLEDs) for lighting applications include improving efficiency and stability of the devices. Phosphorescent dyes based on iridium have been used to achieve high efficiency OLEDs. Other classes of phosphorescent dyes that have been explored in the past include platinum- and europium-based materials, and there have been few successful efforts to design phosphorescent dyes based on other heavy metals. Therefore, there is a need for a new class of materials that can enable devices having improved efficiency and stability.

BRIEF DESCRIPTION

In one aspect, the present invention relates to monodentate gold ethynyl complexes that display phosphorescence at room temperature. Complexes having a gold-carbon bond and a gold-phosphorous bond, and more specifically, complexes of formula I, may be useful for optoelectronic devices

wherein $Ar^1$ and $Ar^2$ are independently monocyclic or polycyclic aryl, unsubstituted or substituted with one or more alkyl, alkenyl, alkoxy, aryl, aryloxy, fluoro, fluoroalkyl, or perfluoroalkyl, and R is substituted or unsubstituted aryl. Accordingly, in another aspect, the present invention relates to optoelectronic devices that include a monodentate gold ethynyl complex of formula I.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
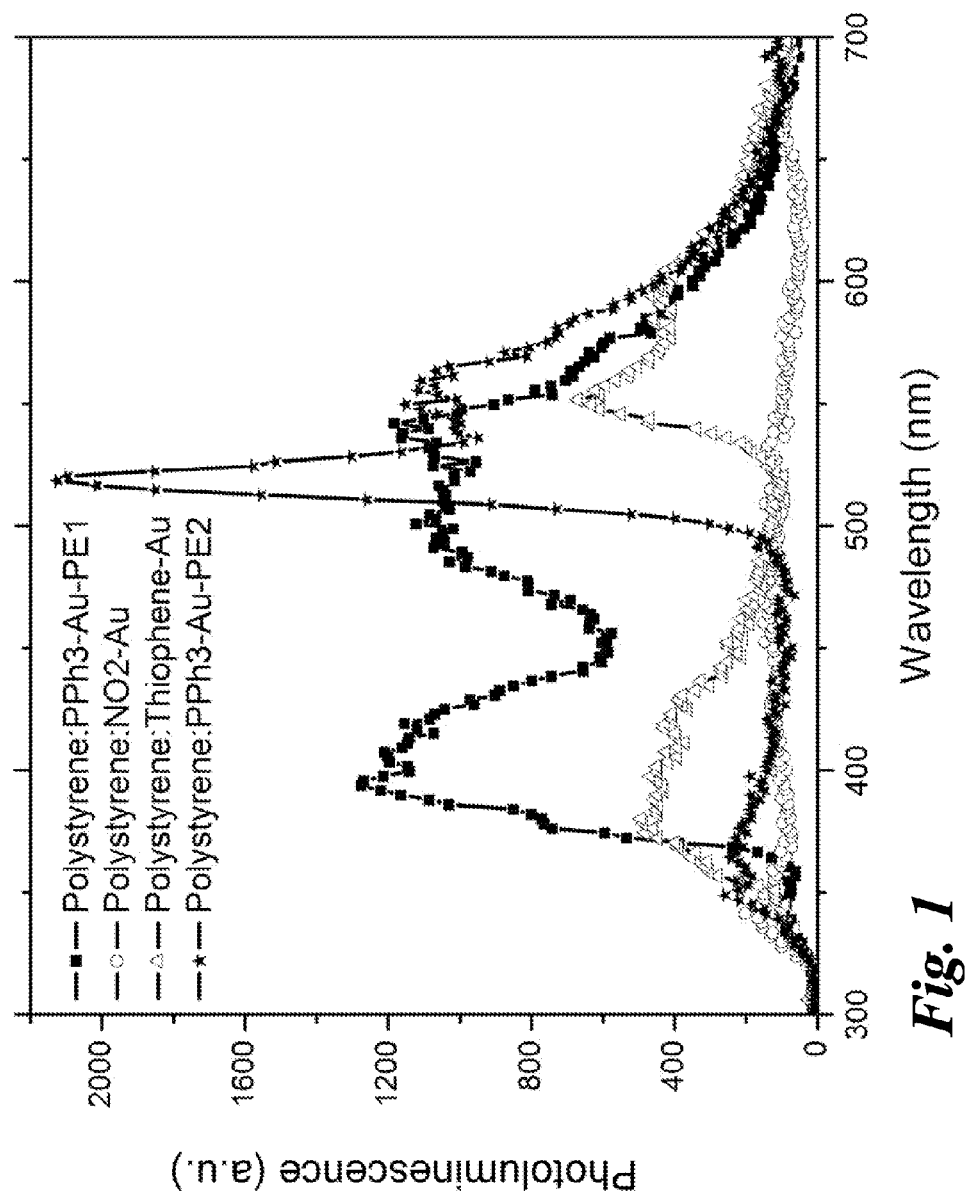
FIG. 1 shows steady state photoluminescence (PL) spectra of thin films of gold ethynyl complexes diluted in a polystyrene matrix.

Gold ethynyl complexes of formula I include divalent aryl group $Ar^2$ connected through a first ethynyl group to monovalent group $Ar^1$ and through a second ethynyl group to —$AuPR_3$. In many embodiments, the $PR_3$ ligand is $PPh_3$. Aryl group $Ar^1$ may be monovalent monocyclic or polycyclic aryl, unsubstituted or substituted with one or more alkyl, alkenyl, alkoxy, aryl, aryloxy, fluoro, fluoroalkyl, or perfluoroalkyl. Aryl group $Ar^2$ may be divalent monocyclic or polycyclic aryl, unsubstituted or substituted with one or more alkyl, alkenyl, alkoxy, aryl, aryloxy, fluoro, fluoroalkyl, or perfluoroalkyl. The monocyclic or polycyclic groups and substituents form are selected independently for $Ar^1$ and $Ar^2$.

In particular embodiments, $Ar^1$ and $Ar^2$ are independently monocyclic aryl, unsubstituted or substituted with one or more alkyl, alkenyl, alkoxy, aryl, aryloxy, fluoro, fluoroalkyl, or perfluoroalkyl. In some embodiments, $Ar^1$ is unsubstituted monocyclic aryl, particularly phenyl. In other embodiments, $Ar^1$ is unsubstituted polycyclic aryl, particularly fluorenyl. In yet other embodiments, $Ar^2$ is unsubstituted monocyclic aryl, particularly phenyl.

Specific examples of monodentate gold ethynyl complexes according the present invention are

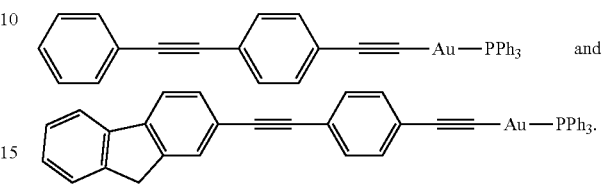

Compounds of formula I may be prepared by reacting a precursor ethynyl compound of formula II with a halo-(triphenylphosphine) gold(I) compound, as shown in Scheme 1.

Scheme 1

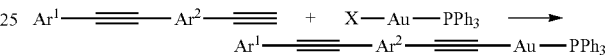

wherein $Ar^1$ and $Ar^2$ are as defined above and X is chloro, bromo or fluoro.

The reaction may proceed at room temperature, typically under basic conditions.

Optoelectronic devices according to the present invention include, but are not limited to, organic light emitting diodes (OLEDs).

An OLED device includes, in the simplest case, an anode layer and a corresponding cathode layer with an organic electroluminescent layer disposed between said anode and said cathode. When a voltage bias is applied across the electrodes, electrons are injected by the cathode into the electroluminescent layer while electrons are removed from (or "holes" are "injected" into) the electroluminescent layer from the anode. Light emission occurs as holes combine with electrons within the electroluminescent layer to form singlet or triplet excitons, light emission occurring as singlet and/or triplet excitons decay to their ground states via radiative decay.

Other components which may be present in an OLED in addition to the anode, cathode and light emitting material include a hole injection layer, an electron injection layer, and an electron transport layer. The electron transport layer need not be in direct contact with the cathode, and frequently the electron transport layer also serves as a hole locking layer to prevent holes migrating toward the cathode. Additional components which may be present in an organic light-emitting device include hole transporting layers, hole transporting emission (emitting) layers and electron transporting emission (emitting) layers.

The organic electroluminescent layer, i.e., the emissive layer, is a layer within an organic light emitting device which when in operation contains a significant concentration of both electrons and holes and provides sites for exciton formation and light emission. A hole injection layer is a layer in contact with the anode which promotes the injection of holes from the anode into the interior layers of the OLED; and an electron injection layer is a layer in contact with the cathode that promotes the injection of electrons from the cathode into the OLED; an electron transport layer is a layer which facilitates conduction of electrons from the cathode and/or the electron injection layer to a charge recombination site. During operation of an organic light emitting device comprising an electron transport layer, the majority of charge carriers (i.e. holes and electrons) present in the electron transport layer are electrons and light emission can occur through recombination of holes and electrons present in the emissive layer. A hole transporting layer is a layer which when the OLED is in operation facilitates conduction of holes from the anode and/or the hole injection layer to charge recombination sites and which need not be in direct contact with the anode. A hole transporting emission layer is a layer in which when the OLED is in operation facilitates the conduction of holes to charge recombination sites, and in which the majority of charge carriers are holes, and in which emission occurs not only through recombination with residual electrons, but also through the transfer of energy from a charge recombination zone elsewhere in the device. An electron transporting emission layer is a layer in which when the OLED is in operation facilitates the conduction of electrons to charge recombination sites, and in which the majority of charge carriers are electrons, and in which emission occurs not only through recombination with residual holes, but also through the transfer of energy from a charge recombination zone elsewhere in the device.

Materials suitable for use as the anode have a bulk conductivity of preferred about 1000 ohms per square, as measured by a four-point probe technique. Indium tin oxide (ITO) is frequently used as the anode because it is substantially transparent to light transmission and thus facilitates the escape of light emitted from electro-active organic layer. Other materials, which may be utilized as the anode layer, include tin oxide, indium oxide, zinc oxide, indium zinc oxide, zinc indium tin oxide, antimony oxide, and mixtures thereof.

Materials suitable for use as the cathode include general electrical conductors including, but not limited to metals and metal oxides such as ITO etc which can inject negative charge carriers (electrons) into the inner layer(s) of the OLED. Various metals suitable for use as the cathode include K, Li, Na, Cs, Mg, Ca, Sr, Ba, Al, Ag, Au, In, Sn, Zn, Zr, Sc, Y, elements of the lanthanide series, alloys thereof, and mixtures thereof. Suitable alloy materials for use as the cathode layer include Ag—Mg, Al—Li, In—Mg, Al—Ca, and Al—Au alloys. Layered non-alloy structures may also be employed in the cathode, for example, a thin layer of calcium metal such as calcium, or a metal fluoride, such as LiF, covered by a thicker layer of a metal, such as aluminum or silver. In particular, the cathode may be composed of a single metal, and especially of aluminum metal.

Materials suitable for use in the electron transport layer include poly(9,9-dioctyl fluorene), tris(8-hydroxyquinolato) aluminum (Alq$_3$), 2,9-dimethyl-4,7-diphenyl-1,1-phenanthroline, 4,7-diphenyl-1,10-phenanthroline, 2-(4-biphenylyl)-5-(4-t-butylphenyl)-1,3,4-oxadiazole, 3-(4-biphenylyl)-4-phenyl-5-(4-t-butylphenyl)-1,2,4-triazole, 1,3,4-oxadiazole-containing polymers, 1,3,4-triazole-containing polymers, quinoxaline-containing polymers, and cyano-PPV.

Materials suitable for use in hole transporting layers include 1,1-bis((di-4-tolylamino)phenyl)cyclohexane, N,N'-bis(4-methylphenyl)-N,N'-bis(4-ethylphenyl)-(1,1'-(3,3'-dimethyl)biphenyl)-4,4'-diamine, tetrakis-(3-methylphenyl)-N,N,N',N'-2,5-phenylenediamine, phenyl-4-N,N-diphenylaminostyrene, p-(diethylamino)benzaldehyde diphenylhydrazone, triphenylamine, 1-phenyl-3-(p-(diethylamino)styryl)-5-(p-(diethylamino)phenyl)pyrazoline, 1,2-trans-bis(9H-carbazol-9-yl)cyclobutane, N,N,N',N'-tetrakis (4-methylphenyl)-(1,1'-biphenyl)-4,4'-diamine, copper phthalocyanine, polyvinylcarbazole, (phenylmethyl)polysilane; poly(3,4-ethylendioxythiophene) (PEDOT), polyaniline, polyvinylcarbazole, triaryldiamine, tetraphenyldiamine, aromatic tertiary amines, hydrazone derivatives, carbazole derivatives, triazole derivatives, imidazole derivatives, oxadiazole derivatives having an amino group, and polythiophenes as disclosed in U.S. Pat. No. 6,023,371

Materials suitable for use in the light emitting layer along with the compounds of formula I include electroluminescent polymers such as polyfluorenes, preferably poly(9,9-dioctyl fluorene) and copolymers thereof, such as poly(9,9'-dioctylfluorene-co-bis-N,N'-(4-butylphenyl)diphenylamine) (F8-TFB); poly(vinylcarbazole) and polyphenylenevinylene and their derivatives. Small molecule host materials such as N,N'-dicarbazolyl-3,5-benzene (mCP), N,N'-dicarbazolyl-4-4'-biphenyl (CBP), host materials disclosed in US2011/0006670, publication date 13 Jan. 2011, assigned to Konica Minolta Holdings, Inc., and silicon-containing materials described by Ren, et al. (Chemistry of Materials 2004 16 (23), 4743-4747) may also be used. The light emitting layer may include a blue, yellow, orange, green or red phosphorescent dye or metal complex, in addition to the gold ethynyl complexes of formula I, for example, tris(1-phenylisoquinoline) iridium (III) (red dye), tris(2-phenylpyridine) iridium (green dye) and Iridium (III) bis(2-(4,6-difluorephenyl)pyridinato-N,C2) (blue dye). Commercially available electrofluorescent and electrophosphorescent metal complexes from ADS (American Dyes Source, Inc.) may also be used. ADS green dyes include ADS060GE, ADS061GE, ADS063GE, and ADS066GE, ADS078GE, and ADS090GE. ADS blue dyes include ADS064BE, ADS065BE, and ADS070BE. ADS red dyes include ADS067RE, ADS068RE, ADS069RE, ADS075RE, ADS076RE, ADS067RE, and ADS077RE.

EXAMPLE 1

Preparation of 4'-(2-phenyl acetylene)phenyl acetylene gold triphenyl phosphine (PPh3-Au-PE2)

To a 100 mL round bottom flask was added 4'-(2-phenyl acetylene)phenyl acetylene (0.108 g, 0.535 mmoles), chloro (triphenylphosphine) gold(I) (0.250 g, 0.504 mmoles) and 40 mL of methanol. This mixture was stirred at room temperature under nitrogen then 350 mg of sodium hydroxide dissolved in 20 mL of methanol was added. The mixture became clear after 1 hour, then a white precipitate formed. After 18 hours, the reaction mixture stirring was stopped and the precipitate allowed to settle. The supernatant which contained the product was separated by decanting and the white solid washed with 20 mL of additional methanol. The liquid layers were combined and concentrated to provide an off white solid (0.30 g, 0.455 mmoles, 90%) which was pure by tlc. $^1$H NMR spectrum 7.31-7.38 complex multiplet, 3H and 7.41-7.62 complex multiplet, 24H.

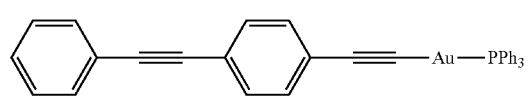

PPh3-Au-PE2

EXAMPLE 2

Preparation of 4-(2-thienyl)-phenyl acetylene gold triphenyl phosphine (Thiophene-Au)

The same method as Example 1 was used, starting with 4-(2-thienyl)phenyl acetylene as the alkyne. A pale yellow solid was isolated. $^1$H NMR spectrum 7.03-7.10 dd, 1H, 7.22-7.34 dd, 2H, 7.42-7.62 complex multiplet, 22H

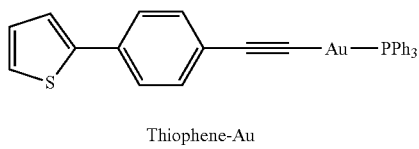

Thiophene-Au

EXAMPLE 3

Preparation of 4(2-fluorenyl acetylene)phenyl acetylene gold triphenyl phosphine The same method as Example 1 was used, starting with 4-(2-fluorenyl acetylene)phenyl acetylene. However, the resulting solid was washed with 50 mL of warm solution of hexanes-ethyl acetate (90:10) to remove traces of starting material, resulting in an off white to cream colored solid. $^1$H NMR spectrum 7.34, t 1H, 7.41 t, 1H, 7.42-7.60 complex multiplet 24H, 7.71-7.62 multiplet, 3H.

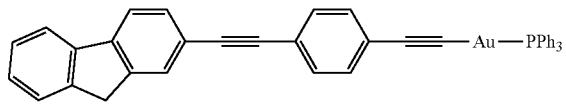

EXAMPLE 4

Preparation of 2-(4-Nitrophenyl)acetylene gold triphenyl phosphine (NO2-Au)

The same method as Example 1 was used, starting with 4-nitrophenyl acetylene. A pale yellow solid was isolated and then washed several times with methanol to yield a pale yellow solid. $^1$H NMR spectrum 7.46-7.63 complex multiplet, 17H, 8.12-8.16 dd, 2H.

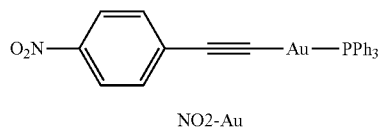

NO2-Au

EXAMPLE 5

Optoelectronic Properties

Steady state photoluminescence of the gold-ethynyl compounds of Examples 1 (PPh3-Au-PE2), 2 (Thiophene-Au), and 4(NO2-Au), and phenyl acetylene gold triphenyl phosphine (PPh3-Au-PE1) was measured using thin films formed from dispersions of the compounds in a polystyrene matrix.

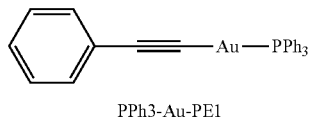

PPh3-Au-PE1

All of the compounds had a broad emission spectrum ranging from 320 nm to 650 nm. Such broad emission spectrum corresponds to white light. Emission spectra are shown in FIG. 1. Delayed photoluminescence of the compound of Example 1 was studied under liquid nitrogen conditions to differentiate the emission from triplets and singlet excitons.

Figure 2:
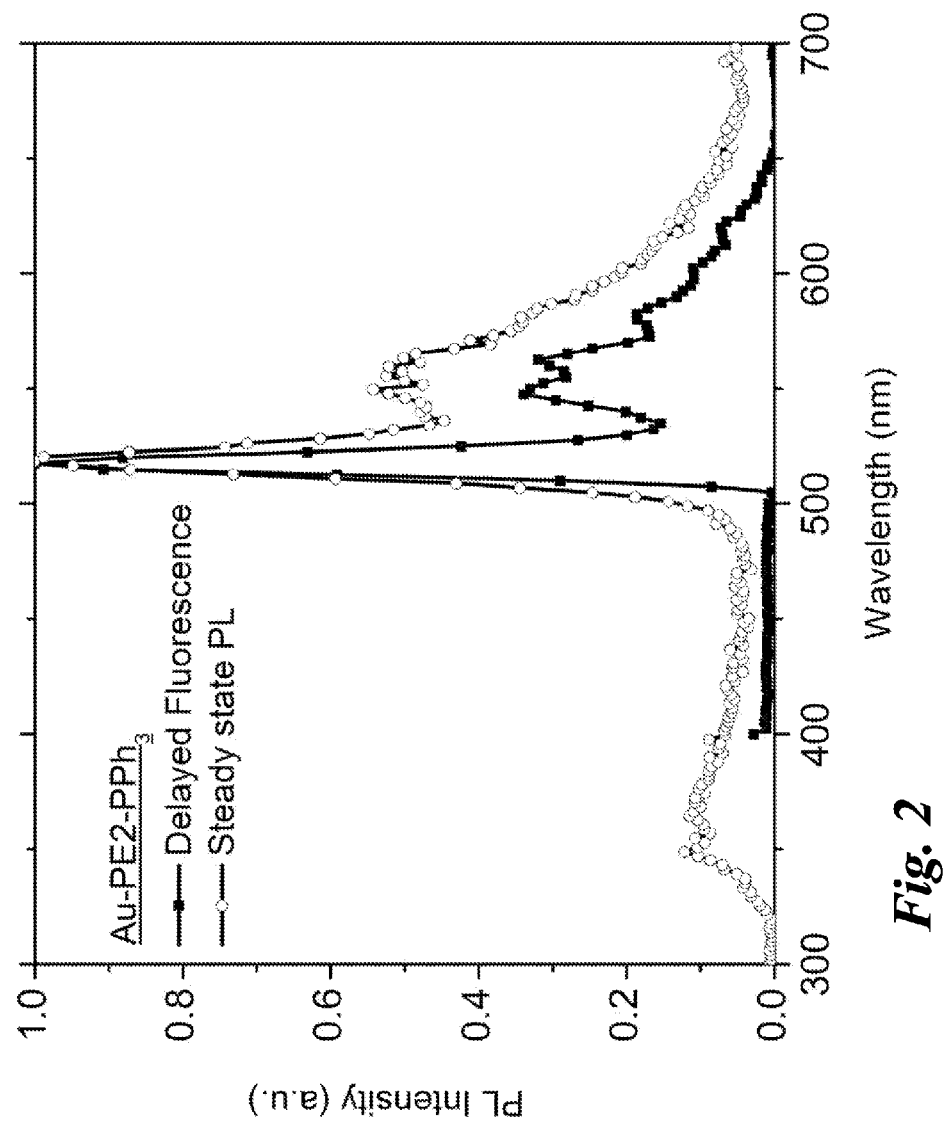
FIG. 2 shows a room temperature steady-state PL spectrum and a low temperature delayed fluorescence spectrum for the gold ethynyl complex of Example 1.

FIG. 2 shows a steady state photoluminescence (PL) spectrum and low temperature delayed PL spectrum for the gold ethynyl of Example 1. Phosphorescence lifetimes are in microsecond to millisecond range while fluorescence decay lifetime is in nanoseconds. The microsecond delayed fluorescence signal observed at 500 nm was attributed to phosphorescence. The phosphorescence signal was also observed at room temperature implying that Au-ethynyl compounds demonstrate room temperature phosphorescence. Besides room temperature phosphorescence, room temperature fluorescence was observed at 350 nm. This is advantageous because a single dye molecule can generate both blue and green light.

In the context of the present invention, alkyl is intended to include linear, branched, or cyclic hydrocarbon structures and combinations thereof, including lower alkyl and higher alkyl. Preferred alkyl groups are those of $C_{20}$ or below. Lower alkyl refers to alkyl groups of from 1 to 6 carbon atoms, preferably from 1 to 4 carbon atoms, and includes methyl, ethyl, n-propyl, isopropyl, and n-, s- and t-butyl. Higher alkyl refers to alkyl groups having seven or more carbon atoms, preferably 7-20 carbon atoms, and includes n-, s- and t-heptyl, octyl, and dodecyl. Cycloalkyl is a subset of alkyl and includes cyclic hydrocarbon groups of from 3 to 8 carbon atoms. Examples of cycloalkyl groups include cyclopropyl, cyclobutyl, cyclopentyl, and norbornyl. Alkenyl and alkynyl refer to alkyl groups wherein two or more hydrogen atoms are replaced by a double or triple bond, respectively.

Aryl and heteroaryl mean a 5- or 6-membered aromatic or heteroaromatic ring containing 0-3 heteroatoms selected from nitrogen, oxygen or sulfur; a bicyclic 9- or 10-membered aromatic or heteroaromatic ring system containing 0-3 heteroatoms selected from nitrogen, oxygen or sulfur; or a tricyclic 13- or 14-membered aromatic or heteroaromatic ring system containing 0-3 heteroatoms selected from nitrogen, oxygen or sulfur. The aromatic 6- to 14-membered carbocyclic rings include, for example, benzene, naphthalene, indane, tetralin, and fluorene; and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Polycyclic aryl groups are those derived from polycyclic aromatic hydrocarbons (PAH), and particularly, fused systems (fused carbocycles), that is, having at least two rings of five or more members and containing only "ortho" or "ortho- and peri-" fusions. Examples of these include, but are not limited to, naphthalene, fluorene, phenanthrene, anthracene, pyrene and perylene. Likewise, polycyclic heteroaryl groups are those derived from polycyclic heteroaromatic compounds, particularly, fused systems (fused heterocycles), such as carbazole, phenothiazine, and thianthrene.

Arylalkyl means an alkyl residue attached to an aryl ring. Examples are benzyl and phenethyl. Heteroarylalkyl means an alkyl residue attached to a heteroaryl ring. Examples include pyridinylmethyl and pyrimidinylethyl. Alkylaryl means an aryl residue having one or more alkyl groups attached thereto. Examples are tolyl and mesityl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, and cyclohexyloxy. Lower alkoxy refers to groups containing one to four carbons.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, and benzyloxycarbonyl. Lower-acyl refers to groups containing one to four carbons.

Heterocycle means a cycloalkyl or aryl residue in which one or two of the carbon atoms is replaced by a heteroatom such as oxygen, nitrogen or sulfur. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, and tetrahydrofuran.

Substituted refers to residues, including, but not limited to, alkyl, alkylaryl, aryl, arylalkyl, and heteroaryl, wherein up to three H atoms of the residue are replaced with lower alkyl, substituted alkyl, alkenyl, substituted alkenyl, aryl, substituted aryl, haloalkyl, alkoxy, carbonyl, carboxy, carboxalkoxy, carboxamido, acyloxy, amidino, nitro, halo, hydroxy, $OCH(COOH)_2$, cyano, primary amino, secondary amino, acylamino, alkylthio, sulfoxide, sulfone, phenyl, benzyl, phenoxy, benzyloxy, heteroaryl, or heteroaryloxy.

Haloalkyl refers to an alkyl residue, wherein one or more H atoms are replaced by halogen atoms; the term haloalkyl includes perhaloalkyl. Examples of haloalkyl groups that fall within the scope of the invention include $CH_2F$, $CHF_2$, and $CF_3$ While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A monodentate gold ethynyl complex of formula I

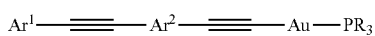

wherein $Ar^1$ and $Ar^2$ are independently monocyclic or polycyclic aryl, unsubstituted or substituted with one or more alkyl, alkenyl, alkoxy, aryl, aryloxy, fluoro, fluoroalkyl, or perfluoroalkyl; and R is substituted or unsubstituted aryl.

2. A monodentate gold ethynyl complex according to claim 1, wherein $Ar^1$ and $Ar^2$ are independently monocyclic aryl, unsubstituted or substituted with one or more alkyl, alkenyl, alkoxy, aryl, aryloxy, fluoro, fluoroalkyl, or perfluoroalkyl.

3. A monodentate gold ethynyl complex according to claim 1, wherein $Ar^1$ is unsubstituted monocyclic aryl.

4. A monodentate gold ethynyl complex according to claim 1, wherein $Ar^1$ is phenyl.

5. A monodentate gold ethynyl complex according to claim 1, wherein $Ar^1$ is unsubstituted polycyclic aryl.

6. A monodentate gold ethynyl complex according to claim 1, wherein $Ar^1$ is fluorenyl.

7. A monodentate gold ethynyl complex according to claim 1, wherein $Ar^2$ is unsubstituted monocyclic aryl.

8. A monodentate gold ethynyl complex according to claim 1, wherein $Ar^2$ is phenyl.

9. A monodentate gold ethynyl complex according to claim 1, of formula

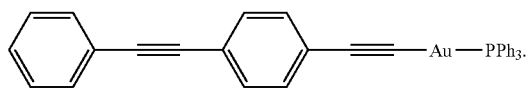

10. A monodentate gold ethynyl complex according to claim 1, of formula

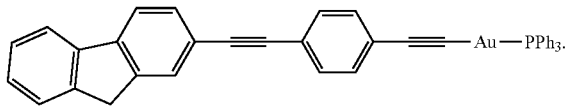

11. An optoelectronic device comprising a monodentate gold ethynyl complex of formula I

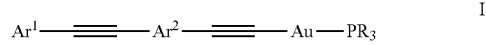

wherein $Ar^1$ and $Ar^2$ are independently monocyclic or polycyclic aryl, unsubstituted or substituted with one or more alkyl, alkenyl, alkoxy, aryl, aryloxy, fluoro, fluoroalkyl, or perfluoroalkyl; and R is substituted or unsubstituted aryl.

12. An optoelectronic device according to claim 11, wherein $Ar^1$ and $Ar^2$ are independently monocyclic aryl, unsubstituted or substituted with one or more alkyl, alkenyl, alkoxy, aryl, aryloxy, fluoro, fluoroalkyl, or perfluoroalkyl.

13. An optoelectronic device according to claim 11, wherein $Ar^1$ is unsubstituted monocyclic aryl.

14. An optoelectronic device according to claim 11, wherein $Ar^1$ is phenyl.

15. An optoelectronic device according to claim 11, wherein $Ar^1$ is unsubstituted polycyclic aryl.

16. An optoelectronic device according to claim 11, wherein $Ar^1$ is fluorenyl.

17. An optoelectronic device according to claim 11, wherein $Ar^2$ is unsubstituted monocyclic aryl.

18. An optoelectronic device according to claim 11, wherein $Ar^2$ is phenyl.

19. An optoelectronic device according to claim 11, wherein the gold ethynyl complex is of formula

20. An optoelectronic device according to claim 11, wherein the gold ethynyl complex is of formula
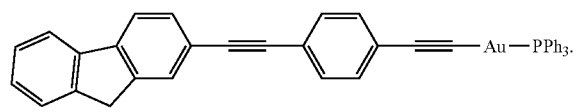
21. An optoelectronic device according to claim 11, comprising an OLED device.
* * * * *